Figure 1:
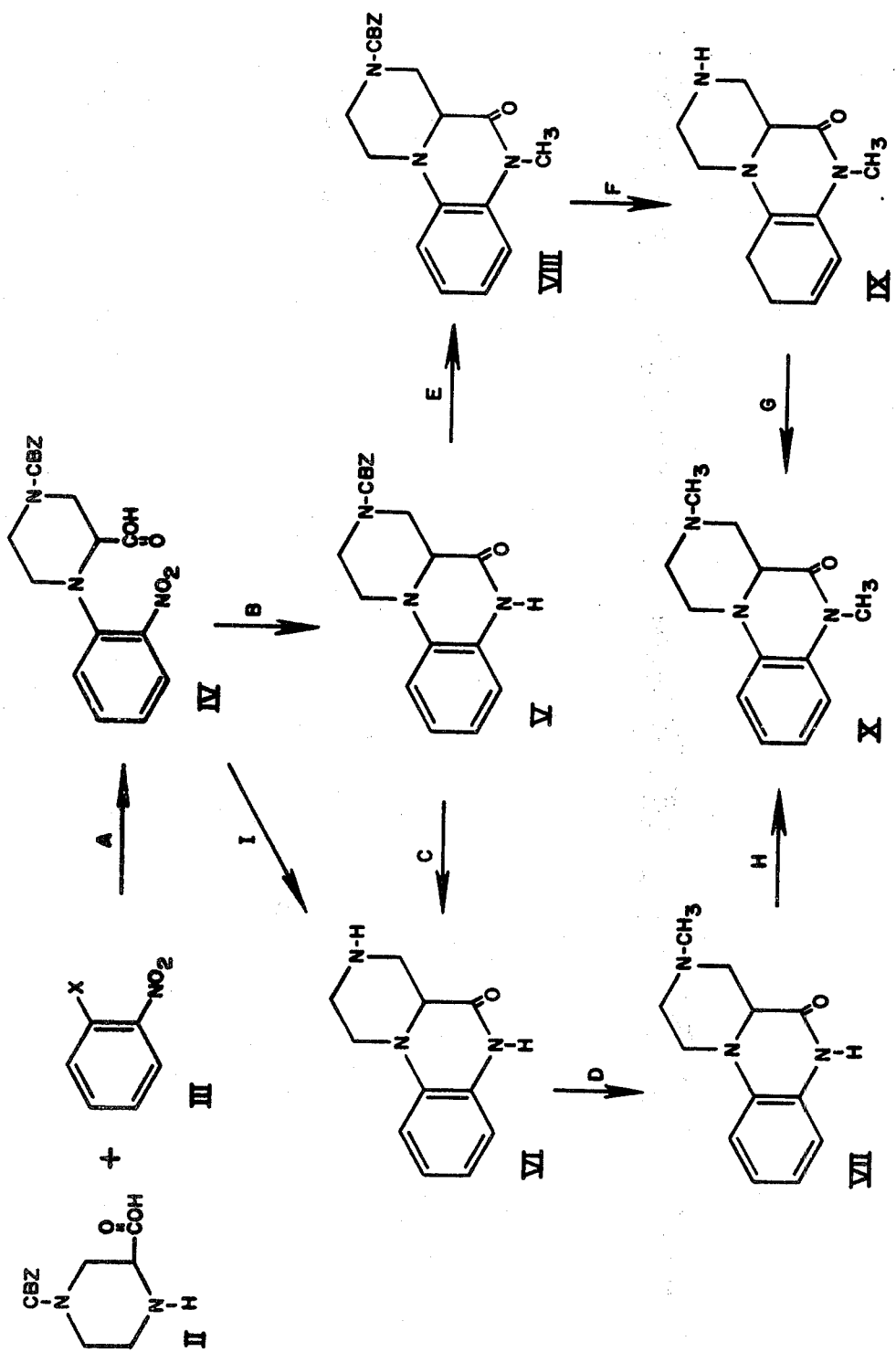

United States Patent [19]

Freed et al.

[11] 4,138,567

[45] Feb. 6, 1979

[54] N-CARBOBENZOXY-N'-(2-NITROPHENYL)-2-PIPERAZINE CARBOXYLIC ACID

[75] Inventors: Meier E. Freed, Paoli; John R. Potoski, Spring City, both of Pa.

[73] Assignee: American Home Products Corporation, New York, N.Y.

[21] Appl. No.: 835,560

[22] Filed: Sep. 22, 1977

Related U.S. Application Data

[60] Division of Ser. No. 752,577, Dec. 20, 1976, Pat. No. 4,089,958, which is a continuation-in-part of Ser. No. 668,872, Mar. 22, 1976, Pat. No. 4,032,639.

[51] Int. Cl.² .................. C07D 241/18; C07D 241/06
[52] U.S. Cl. .................................. 544/388; 544/346; 544/389; 424/250
[58] Field of Search .................... 260/268 PH, 268 C; 544/388

[56] References Cited

U.S. PATENT DOCUMENTS

| 4,032,639 | 6/1977 | Freed ................................. 424/251 |
| 4,089,958 | 5/1978 | Freed et al. ......................... 544/388 |

Primary Examiner—Jose Tovar

[57] ABSTRACT

Compounds of the formula

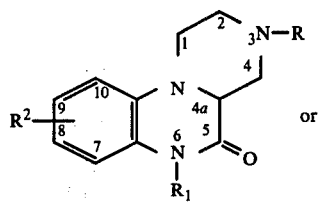

or

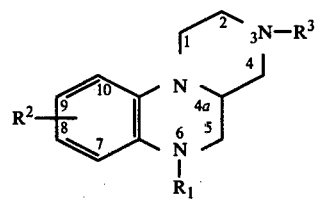

wherein R is hydrogen (lower)alkyl, phen(lower)alkyl, benzoyl(lower)alkyl, or p-halobenzoyl(lower)alkyl; $R^1$ is hydrogen or (lower)alkyl; $R^2$ is hydrogen, (lower)alkyl, (lower)alkoxy, chlorine, fluorine, trifluoromethyl, or amino in the 7-, 8-, or 9-position; $R^3$ is hydrogen, or (lower)alkyl; and $R^4$ is hydrogen, (lower)alkyl, (lower)alkoxy, chlorine, fluorine, or trifluoromethyl in the 7-, 8-, or 9-position; or the non-toxic acid addition salts thereof; exert a hypotensive effect in hypertensive animals.

11 Claims, 1 Drawing Figure

N-CARBOBENZOXY-N'-(2-NITROPHENYL)-2-PIPERAZINE CARBOXYLIC ACID

This is a divisional of application Ser. No. 752,577, filed Dec. 20, 1976, now Pat. No. 4,089,958, issued May 16, 1978, which is a continuation-in-part of Ser. No. 668,872, filed Mar. 22, 1976, now U.S. Pat. No. 4,032,639.

The present invention relates to substituted 2,3,4,4a-tetrahydro-1H-pyrazino[1,2-a]quinoxalin-5(6H)-ones and substituted 2,3,4,4a,5,6,hexahydro-1H-pyrazino[1,2-a]quinoxalines, which compounds have pharmacological activity. Also contemplated by this invention are intermediates used in the synthesis of said compounds, and methods of use.

This invention comprises chemical compounds of the formula

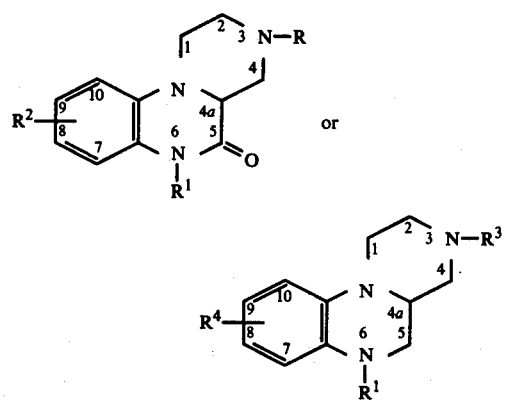

wherein:

R is hydrogen, (lower)alkyl, phen(lower)alkyl, benzoyl(lower)alkyl, or p-halobenzoyl(lower)alkyl;

$R^1$ is hydrogen or (lower)alkyl;

$R^2$ is hydrogen, (lower)alkyl, (lower)alkoxy, chlorine, fluorine, trifluoromethyl, or amino in the 7-, 8-, or 9-position;

$R^3$ is hydrogen or (lower)alkyl; and $R^4$ is hydrogen, (lower)alkyl, (lower)alkoxy, chlorine, fluorine, or trifluoromethyl in the 7-, 8-, or 9-position; or the non-toxic acid addition salts thereof;

The compounds of Formula Ia or Ib exert a hypotensive effect in hypertensive warm-blooded animals, as evidenced by pharmacological evaluation in standard test procedures.

In subgeneric aspects, this invention contemplates the following preferred embodiments:

A compound of Formula Ia wherein R and $R^1$ are each hydrogen and $R^2$ has the meanings defined hereinabove.

The compound of Formula Ia wherein R, $R^1$, and $R^2$ are each hydrogen.

A compound of Formula Ia wherein R is hydrogen, $R^1$ is (lower)alkyl, and $R^2$ has the meanings defined hereinabove.

A compound of Formula Ia wherein R is (lower)alkyl, phen(lower)alkyl, benzoyl(lower)alkyl, or p-halobenzoyl(lower)alkyl; $R^1$ is hydrogen; and $R^2$ has the meanings defined hereinabove.

A compound of Formula Ia wherein R is (lower)alkyl, $R^1$ is hydrogen, and $R^2$ has the meanings defined hereinabove.

A compound of Formula Ib wherein $R^1$ and $R^3$ are each hydrogen and $R^4$ has the meanings defined hereinabove.

The compound of Formula Ib wherein $R^1$, $R^3$, and $R^4$ are each hydrogen.

A compound of Formula Ib wherein $R^1$ is (lower)alkyl, $R^3$ is hydrogen, and $R^4$ has the meanings defined hereinabove.

A compound of Formula Ib wherein $R^1$ is hydrogen, $R^3$ is (lower)alkyl, and $R^4$ has the meanings defined hereinabove.

A compound of Formula Ia wherein R and $R^2$ are each hydrogen and $R^1$ is (lower)alkyl.

A compound of Formula Ia wherein $R^1$ and $R^2$ are each hydrogen and R is (lower)alkyl, phen(lower)alkyl, benzoyl(lower)alkyl, or p-halobenzoyl(lower)alkyl.

A compound of Formula Ia wherein $R^1$ and $R^2$ are each hydrogen and R is (lower)alkyl.

A compound of Formula Ib wherein $R^3$ and $R^4$ are each hydrogen and $R^1$ is (lower)alkyl.

A compound of Formula Ib wherein $R^1$ and $R^4$ are each hydrogen and $R^3$ is (lower)alkyl.

Also within the scope of this invention are the intermediates employed in the synthesis of the compounds of Formula Ia. Such intermediates are:

(a) compounds of the formula:

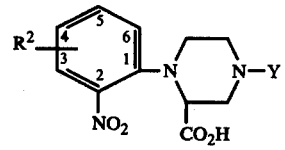

wherein:

Y is (lower)alkyl or carbobenzoxy; and $R^2$ is hydrogen, (lower)alkyl, (lower)alkoxy, chlorine, fluorine, trifluoromethyl, or trifluoroacetamido in the 3-, 4-, or 5-position of the phenyl ring; or the salts thereof;

(b) compounds of the formula:

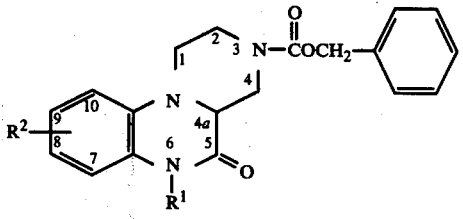

wherein:

$R^1$ is hydrogen or (lower)alkyl; and $R^2$ is hydrogen, (lower)alkyl, (lower)alkoxy, chlorine, fluorine, trifluoromethyl, amino, or trifluoroacetamido in the 7-, 8-, or 9-position;

(c) the compound which is 4-carbobenzoxypiperazine-2-carboxylic acid or the salts thereof.

In the compounds of Formula Ia or Ib, the substituent represented by $R^2$ is substituted in the phenyl ring of the nucleus at either the 7-, 8-, or 9-position. The 9-position is preferred.

As used herein and in the claims the term "(lower)alkyl" means an aliphatic hydrocarbon group containing up to three carbon atoms, i.e. the methyl, ethyl, propyl, or isopropyl groups. The methyl group is especially preferred. The term "(lower)alkoxy" means an aliphatic ether group having up to three carbon atoms, i.e. methoxy, ethoxy, propoxy, or isopropoxy. The methoxy group is especially preferred. The term "phen(lower)alkyl" means a group in which the phenyl group is attached to an aliphatic hydrocarbon chain containing up to three carbon atoms, e.g. the benzyl, phenethyl, or phenpropyl groups. The term "benzoyl(lower)alkyl" means a group in which the benzoyl group is attached to an aliphatic hydrocarbon chain containing up to three carbon atoms, e.g. benzoylmethyl, benzoylethyl, or benzoylpropyl. The term "p-halobenzoyl(lower)alkyl" means a benzoyl(lower)alkyl group in which the phenyl moiety thereof is substituted in the para position by a fluorine or chlorine atom. The p-fluorobenzoylpropyl group is especially preferred. The term "o-nitrohalobenzene" means nitrobenzene containing a fluorine, chlorine, or bromine atom in the ortho position.

The general method of synthesis of the compounds of Formula Ia is illustrated schematically in FIG. I of the annexed drawing which depicts the preparation of 2,3,4,4a-tetrahydro-1H-pyrazino[1,2-a]quinoxalin-5(6H)-one and the derivatives thereof containing a 3-methyl and/or 6-methyl group. In FIG. I, the symbol CBZ means a carbobenzoxy group:

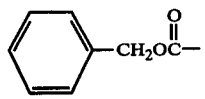

while X represents a chlorine, fluorine, or bromine atom.

Referring now to FIG. I, wherein the compounds are assigned Roman numerals for identification, in Process A, 4-carbobenzoxypiperazine-2-carboxylic acid (II) is condensed with a o-nitrohalobenzene (III), to afford a 4-carbobenzoxy-1-(o-nitrophenyl)piperazine-2-carboxylic acid (IV). The reaction is carried out in an inert organic solvent, such as dimethylsulfoxide, in the presence of a base, such as triethylamine at a temperature from about 20° to about 100° C., preferably 90° C. The o-nitrofluorobenzenes are preferred starting materials.

The intermediate IV is cyclized to a 3-carbobenzoxy-2,3,4,4a-tetrahydro-1H-pyrazino[1,2-a]quinoxalin-5(6H)-one (V) by a two-step process involving reduction of the nitro group to the amino group followed by cyclization. The reduction step is preferably performed by treating a water solution of the sodium or other soluble salt of the nitro-acid (IV) with a suitable reducing agent, such as sodium dithionite. The amino-acid thus produced is cyclized by adjusting the pH of the solution to about 7.5 or less (preferably a pH of about 3).

The 3-carbobenzoxy protecting group is removed from a 3-carbobenzoxy-2,3,4,4a-tetrahydro-1H-pyrazino[1,2-a]quinoxalin-5(6H)-one (V) by catalytic hydrogenation (Process C) to afford a 2,3,4,4a-tetrahydro-1H-pyrazino[1,2-a]quinoxalin-5(6H)-one (VI). The hydrogenation is carried out in an inert solvent, such as ethanol, in the presence of a catalyst, such as 10% palladium on carbon, at a pressure of from about 1 atm. to about 3 atm., preferably about 3 atm.

If desired the hydrogenation may be performed in the presence of hydrogen chloride which provides the product as the acid addition salt. Alternatively, intermediate IV can be reductively cyclized by catalytic hydrogenation (Raney nickel), underwhich conditions the carbobenzoxy group is also removed, to afford the product VI directly (Process I).

When it is desired to prepare a product containing a substituent at the 3-position, a 2,3,4,4a-tetrahydro-1H-pyrazino[1,2-a]quinoxalin-5(6H)-one (VI) is treated with a suitable alkylating agent (Process D), for example, an alkyl halide. The reaction is performed in an inert solvent, such as ethanol, preferably in the presence of a weak base, such as potassium carbonate. Other alkylating agents, such as the tosylate derivatives, will be apparent to those skilled in the art.

When it is desired to prepare a compound containing a substituent in the 6-position, a 3-carbobenzoxy-2,3,4,4a-tetrahydro-1H-pyrazino[1,2-a]quinoxalin-5(6H)-one (V) is alkylated at the 6-position (Process E) and then catalytically hydrogenated (Process F) to remove the protecting 3-carbobenzoxy group. The alkylation is effected by contacting the intermediate (V) with a strong base, e.g. sodium hydride, in an inert solvent, e.g. dimethyl formamide, and then adding the alkylating agent, e.g. a (lower)alkyl halide or tosylate. The 3-carbobenzoxy protecting group is removed by the methods as hereinabove discussed.

When it is desired to prepare a product (X) containing substituents at both the 3- and 6- positions, the intermediate VII can be alkylated in the 6-position (Process H) or the intermediate IX can be alkylated in the 3-position (Process G) using the techniques hereinbefore described.

While the above method of synthesis has been described by reference to FIG. I which illustrates the preparation of 2,3,4,4a-tetrahydro-1H-pyrazino[1,2-a]quinoxalin-5(6H)-one and derivatives thereof containing a 3-methyl and/or 6-methyl group, it will be apparent to those skilled in the art of chemistry that any of the compounds as variously substituted within the scope of Formula Ia may be prepared by this method or by modification of this method which would be obvious to those skilled in the art. Thus, compounds of Formula Ia wherein $R^2$ is a group other than hydrogen may be prepared by employing the appropriately substituted o-nitrohalobenzene in Process A and using the intermediates formed therefrom in the subsequent processes.

When it is desired to prepare a compound wherein $R^2$ is amino, the amino group in the starting nitrobenzene compound can be blocked to prevent side reactions during the synthesis. The blocking group can be removed by standard techniques at a later stage of the process. The trifluoroacetyl group is conveniently used as a blocking group.

Compounds where R is phen(lower)alkyl, benzoyl(lower), alkyl, or p-halobenzoyl(lower)alkyl may be prepared by employing the appropriately substituting alkylating agent in Processes D, E, H, or G, described above.

The compounds of Formula Ia wherein R is (lower)alkyl, are conveniently prepared by an alternate process in which a 4-(lower)alkylpiperazine-2-carboxylic acid is employed in place of 4-carbobenzoxypiperazine-2-carboxylic acid (II) in Process A described above. Reduction of the nitro group of the product thus formed followed by cyclization (as in Process B, described above) directly gives the desired 3-(lower)alkyl 2,3,4,4a-tetrahydro-1H-pyrazino[1,2-a]quinoxalin-5(6H)-ones without the need for blocking and deblocking the piperazine nitrogen.

In the method of synthesis depicted in FIG. I, the carbobenzoxy group is employed as a blocking group to protect the reactive nitrogen of the piperazine ring of the intermediates. It will be obvious to those skilled in the art that any conventional blocking group useful for protecting a secondary amino group may be employed, for example, the benzhydryl or benzyl group.

In general, the compounds of Formula Ia are converted to the compounds of Formula Ib by reduction of the lactam carbonyl group of an appropriate intermediate or product. This can be effected using a reducing agent which will reduce the lactam carbonyl without reducing other substituents. A particularly useful method is to treat 2,3,4,4a-tetrahydro-1H-pyrazino[1,2-a]quinoxalin-5(6H)-one or derivatives thereof with lithium aluminum hydride in an inert solvent at an elevated temperature, for example, refluxing tetrahydrofuran.

4-Carbobenzoxypiperazine-2-carboxylic acid (II) employed as a starting material in Process A is prepared from piperazine-2-carboxylic acid in three steps: (a) treating said acid, as the dihydrochloride, with cupric carbonate in water to form the cupric ion chelate; (b) treating the chelate with benzylchloroformate in acetone-water to introduce the carbobenzoxy group; and (c) treating the 3-carbobenzoxypiperazine-2-carboxylic acid, copper chelate with hydrochloric acid and hydrogen sulfide to destroy the chelate. The product is isolated as the hydrochloride salt.

The o-nitrohalobenzenes employed as starting materials in the process described above are either known compounds or may be prepared from known compounds by methods which will be apparent to one skilled in the art of chemistry. The o-nitrofluorobenzenes are preferred starting materials since the fluorine atom is more easily replaced than chlorine or bromine.

Since the compounds of Formula Ia or Ib possess an asymmetric carbon atom optical enantiomorphs are possible, and the compounds of the invention may be in the form of the pure enantiomorph or mixtures thereof, such as the racemates.

The compounds of Formula Ia or Ib may be obtained in the form of the pure enantiomorph either by resolving a desired racemic product or by resolving a racemic starting material or intermediate at any convenient stage of the synthesis. Methods of carrying out the resolution are well known in the art of chemistry. For example, the desired racemate may be treated with an optically active carboxylic acid and the optically active addition salts may be separated by standard techniques.

The compounds of Formula Ia and Ib as obtained in the processes depicted in FIG. I, and the appropriate intermediates thereto, may be isolated and purified in a conventional manner. It is furthermore appreciated that in the various processes hereinbefore described, factors such as solvents or temperatures are not critical and the selection of a temperature or solvent for a particular process will be apparent to one skilled in the art.

The compounds of Formula Ia or Ib may exist either in the form of the free base or the acid addition salt. Methods for converting one such form to another will be obvious to one skilled in the art of chemistry.

The amino acids, 4-carbobenzoxypiperazine-2-carboxylic acid and the 4-(substituted)-1-(o-nitrophenyl)-piperazine-2-carboxylic acids, employed as intermediates for preparing the compounds of Formula Ia or Ib may exist either in the acid, base, or zwitterion form, and methods for converting one such form to another will be apparent to those skilled in the art.

For pharmacological use, the compounds of Formula Ia or Ib may be administered in the form of an acid addition salt of a non-toxic organic or inorganic acid. The salts may be prepared by methods well known in the art. Appropriate salts are those formed from the following acids: hydrochloric, hydrobromic, sulfonic, sulfuric, phosporic, nitric, maleic, fumaric, benzoic, ascorbic, pamoic, succinic, methanesulfonic, acetic, propionic, tartaric, citric, lactic, malic, mandelic, cinnamic, palmitic, itaconic, and benzenesulfonic.

In its method of use aspect, this invention provides a method for relieving hypertension in warm-blooded animals which comprises administering to an animal in need thereof a hypotensive effective amount of a compound selected from the group consisting of:

2,3,4,4a-tetrahydro-1H-pyrazino[1,2-a]quinoxalin-5(6H)-one;

2,3,4,4a-tetrahydro-6-methyl-1H-pyrazino[1,2-a]quinoxalin-5(6H)-one;

2,3,4,4a-tetrahydro-9-methoxy-1H-pyrazino[1,2-a]quinoxalin-5(6H)-one;

7-chloro-2,3,4,4a-tetrahydro-1H-pyrazino[1,2-a]quinoxalin-5(6H)-one;

8-chloro-2,3,4,4a-tetrahydro-1H-pyrazino[1,2-a]quinoxalin-5(6H)-one;

9-chloro-2,3,4,4a-tetrahydro-1H-pyrazino[1,2-a]quinoxalin-5(6H)-one;

2,3,4,4a-tetrahydro-8-trifluoromethyl-1H-pyrazino[1,2-a]quinoxalin-5(6H)-one;

2,3,4,4a-tetrahydro-9-methyl-1H-pyrazino[1,2-a]quinoxalin-5(6H)-one;

7-fluoro-2,3,4,4a-tetrahydro-1H-pyrazino[1,2-a]quinoxalin-5(6H)-one;

8-fluoro,2,3,4,4a-tetrahydro-1H-pyrazino[1,2-a]quinoxalin-5(6H)-one; or 9-fluoro-2,3,4,4a-tetrahydro-1H-pyrazino[1,2-a]quinoxalin-5(6H)one.

When employed to relieve hypertension, the effective dosage of the compounds of Formula Ia or Ib will vary according to the particular compound being employed, the severity and nature of the hypertension, and the particular subject being treated. In general, with large warm-blooded animals (about 70 kg. body weight) effective results can be achieved by the oral route at a dosage level of from 25 mg. to about 2 g. given as needed, for example every four to six hours. A dose of about 25 mg. to about 500 mg. is preferred. Therapy should be initiated at lower dosages, the dosage thereafter being increased until the desired hypotensive effect is obtained.

When employed as hypotensive agents, the active substances may be administered alone or in combination with pharmaceutically acceptable carriers, the proportion and nature of which are determined by the solubility and chemical properties of the compound selected, the chosen route of administration, and standard pharmaceutical practice. For example, the compounds of Formula Ia or Ib may be administered orally in solid dosage forms, e.g. capsules, tablets, or powders, or in liquid forms, e.g. solutions or suspensions. The compounds may also be injected parenterally in the form of sterile solutions or suspensions. Solid oral forms may contain conventional excipients, for instance: lactose, succrose, magnesium stearate, resins, and like materials. Liquid oral forms may contain various flavoring, coloring, preserving, stabilizing, solublizing or suspending agents. Parenteral preparations are sterile aqueous or nonaqueous solution or suspensions which may contain various preserving, stabilizing, buffering, solubilizing, or suspending agents. If desired, additives, such as saline or glucose may be added to make the solutions isotonic.

The following examples are illustrative of the processes of the invention. All temperatures are in centigrade.

EXAMPLE I

4-Methyl-1-(o-nitrophenyl)piperazine-2-carboxylic acid

A solution of 6.6 g. (0.164 mole) of sodium hydroxide, 28.2 g. (0.165 mole) of ethyl-4-methylpiperazine-2-carboxylate, 20 ml. of water and 200 ml. of ethanol is refluxed for 3 hours. This solution is then added under nitrogen to a hot stirred solution of o-nitrofluorobenzene in 300 ml. of ethanol and 30 ml. of water. The resultant solution is refluxed for 48 hours, cooled and filtered to give 12.8 g. of yellow product, m.p. 222°–225°. Concentration of the mother liquors to ~100 ml. and adjusting the pH to 6 yields an additional 6.6 g. of product. Further concentration of mother liquors gives yet another 3 g. of product. Total yield is 22.4 g., 51.5%. The analytical sample had m.p. 234° dec.

Analysis for: $C_{12}H_{15}N_3O_4.H_2O$: Calculated: C, 50.88; H, 6.05; N, 14.82. Found: C, 51.67; H, 5.95; N, 15.15.

EXAMPLE II 2,3,4,4a-Tetrahydro-3-methyl-1H-pyrazino[1,2-a]quinoxaline-5(6H)-one A mixture of 3.5 g. (0.0135 mole) of 4-methyl-1-(o-nitrophenyl)piperazine-2-carboxylic acid, 2.5 g. (0.025 mole) of potassium bicarbonate, 110 ml. of water, 110 ml. of ethanol and 2½ teaspoons of Raney nickel is hydrogenated in a Parr apparatus for 12 hours at an initial hydrogen pressure of 47 p.s.i. The catalyst is filtered and the filtrate is acidified with dilute hydrochloric acid. The mixture is then basified with sodium hydroxide and extracted with ethylacetate. The extract is dried and concentrated to give 2.3 g. of product. This is treated with 1 equivalent of hydrogen chloride in ethanol. After standing and cooling, filtration gives 2.4 g. of product, as the hydrochloride salt, m.p. 272°–275°. Recrystallization of the salt from ethanol-water gives 1.75 g., m.p. 284°–285° dec.

Analysis for: $C_{12}H_{16}N_3O.\frac{1}{2}H_2O$: Calculated: C, 54.85; H, 6.52; N, 15.99. Found: C, 54.86; H, 6.46; N 15.82.

EXAMPLE III 2,3,4,4,a,5,6-Hexahydro-3-methyl-1H-pyrazino[1,2-a]quinoxaline

A mixture of 7.1 g. of 2,3,4,4a-tetrahydro-3-methyl-1H-pyrazino[1,2-a]quinoxalin-5(6H)-one, 3.5 g. of lithium aluminum hydride and 450 ml. of dry tetrahydrofuran is refluxed for 20 hours under a nitrogen atmosphere. The mixture is cooled and 20 ml. of concentrated ammonium hydroxide is carefully added. The mixture is filtered and the filter cake is washed with isopropanol. The filtrate is concentrated to give 5.7 g. of product as a viscous oil. A 3.5 g. portion is dissolved in acetone and treated with a saturated solution of fumaric acid in acetone. Filtration gives 3.3 g. of the product as the fumaric acid salt, m.p. 178°–188°. Recrystallization from isopropanol gives 2.1 g. of salt, m.p. 186°–188°.

Analysis for: $C_{12}H_{17}N_3.C_4H_4O_4$: Calculated: C, 60.17; H, 6.63; N, 13.16. Found: C, 60.01; H, 6.45; N, 12.68.

EXAMPLE IV

4-Carbobenzoxypiperazine-2-carboxylic Acid, Copper Chelate

To a stirred solution of 40.8 g. of piperazine-2-carboxylic acid, dihydrochloride in 700 ml. of water, is added slowly 48 g. of cupric carbonate. The mixture is heated to boiling, then filtered hot. After cooling the deep blue filtrate is placed in a creased flask equipped with efficient mechanical stirring and 60 g. of sodium bicarbonate is cautiously added with an additional 300 ml. $H_2O$. To the stirred blue copper complex solution is added slowly (about 1 hour) a solution of 45 ml. of benzychloroformate (95%) in 700 ml. of acetone. The mixture was stirred overnight (room temperature) and filtered. The pale blue solid is collected and washed with water (~500 ml), ethanol (~500 ml.), and ether (~500 ml.), then dried to give 60 g. of product, m.p. 222°–228°.

EXAMPLE V

4-Carbobenzoxypiperazine-2-carboxylic Acid, Hydrochloride

The pale blue copper complex (~60 gm.) is placed in a flask equipped with a gas inlet and mechanical stirring. One liter of water containing 60 ml. of concentrated hydrochloric acid is added and gaseous hydrogen sulfide then bubbled into the stirred mixture for 45 minutes at room temperature. The pale blue mixture turned black. When the hydrogen sulfide treatment is completed, the gas inlet is connected to a nitrogen tank and nitrogen is bubbled through the mixture for ½ hour at room temperature to remove remaining hydrogen sulfide. The mixture is then filtered through celite, with suction. The filter cake is washed with a little water (75–100 ml.). The combined filtrates are brought to pH 7 with concentrated NaOH, then concentrated on a rotary evaporator until a white solid precipitated. The mixture is cooled and filtered. The same process is repeated with successive filtrates until there is only a small amount of filtrate volume remaining (~75 to 100 ml. of yellow solution). The collected white solids so obtained is placed in a flask with 1.5 liters of ethanol. The resulting suspension is acidified with ethanolic hydrogen chloride, then stirred for 20 minutes at room temperature and filtered. The filtrate is concentrated to ~350 ml. (crystallization begins) then cooled and filtered to give 26.5 g. of product as the hydrochloride salt, m.p. 209°–212°. The mother liquors are concentrated (~125 ml.) cooled and filtered to yield an additional 6.6 g. of product, m.p. 208°–212°. Further concentration to ~50 ml. yields another 5.0 g. of product, m.p. 208°–211° dec. Total yield is 38.1 g., 63% from piperazine-2-carboxylic acid.

EXAMPLE VI

4-Carbobenzoxy-1-(o-nitrophenyl)piperazine-2-carboxylic acid

A mixture of 12.0 g. (0.04 mole) of 4-carbobenzoxypiperazine-2-carboxylic acid, 8.4 g. (0.06 mole) of o-nitrofluorobenzene, 16 g. of triethylamine and 100 ml. of dimethylsulfoxide is heated at 90° for 8½ hours, cooled, diluted with water (300 ml.) and extracted with ether. The aqueous phase is then acidified with dilute hydrochloric acid and extracted with ether. The combined ether extracts are diluted with 1/3 its volume of pentane. The ether-pentane solution is washed with water, dried (MgSO$_4$) and concentrated to give 14 g. of yellow-orange glassy product. Thin layer chromatography analysis (10% acetic acid in benzene on a silica gel plate) shows 1 main spot with a faint second impurity spot.

EXAMPLE VII

3-Carbobenzoxy-2,3,4,4a-tetrahydro-1H-pyrazino[1,2-a]quinoxalin-5(6H)-one

To a solution of 13 g. of 4-carbobenzoxy-1-(o-nitrophenyl)piperazino-2-carboxylic acid and 11.0 g. of sodium hydroxide in 200 ml. of water is added a solution of 20 g. of sodium hydrosulfite in 200 ml. of H$_2$O. The orange solution gradually turns colorless over a period of 2–3 hours. Dilute hydrochloric acid is added to bring the pH of the solution to about 3. A white precipitate forms. Stirring is continued for about 3–5 minutes, and the pH is raised to about 7 by the addition of 40% sodium hydroxide. Filtration gives 8.6 g. of product, m.p. 125°–140°. The analytical sample on recrystallization from ethyl acetate hexane gave a m.p. 167°–170°.

Analysis for: C$_{19}$H$_{19}$N$_3$O$_3$: Calculated: C, 67.64; H, 5.68; N, 12.46. Found: C, 67.60; H, 5.67; N, 12.44.

EXAMPLE VIII 2,3,4,4a-Tetrahydro-1H-Pyrazino[1,2-a]Quinoxalin-5(6H)-One

A mixture of 3.0 g. of 3-carbobenzoxy-2,3,4,4a-tetrahydro-1H-pyrazino[1,2-a]quinoxalin-5(6H)-one, 2 g. of hydrogen chloride, 3 g. of 10% palladium on carbon and 200 ml. of ethanol is hydrogenated on a Parr apparatus for 18 hours at 46 p. s. i. hydrogen pressure. The catalyst is filtered and the filtrate is concentrated. The residue is recrystallized from ethanol to give 0.55 g. of the product as the hydrogen chloride salt, m.p. 288°–290°.

Analysis for: C$_{11}$H$_{14}$N$_3$OCl: Calculated: C, 55.11; H, 5.87; N, 17.53. Found: C, 54.55; H, 5.80; N, 17.43.

EXAMPLE IX 2,3,4,4a-Tetrahydro-6-Methyl-1H-Pyrazino[1,2-a]Quinoxaline-5(6H)-One To a stirred suspension of 0.87 g. (0.0180 mole) of sodium hydride (50% suspension in nujol) in 50 ml. of dimethyl formamide under a nitrogen atmosphere is added 5.5 g. (0.968 mole) of 3-carbobenzoxy-2,3,4,4a-tetrahydro-1H-pyrazino[1,2-a]quinoxaline-5(6H)-one. The mixture is stirred ½ hours, then to it is added 4.5 g. of methyl iodide in 10 ml. of dimethylformamide. The resultant mixture is stirred for 1 hour, then poured into 100 ml. of water. The aqueous mixture is extracted with methylene chloride, dried (MgSO$_4$) and concentrated to give 5.7 g. of viscous glass. This glass is dissolved in 150 ml. of ethanol containing 0.3 g. of hydrogen chloride and hydrogenated over 5 g. of 10% palladium on carbon for 5½ hours at 45 p. s. i. hydrogen pressure with the temperature about 50°. The catalyst is filtered and the filtrate is concentrated. Recrystallization of the residue from ethanol gives 1.9 g. of product as the hydrochloride salt, m.p. 260°–264°.

Analysis for: C$_{12}$H$_{15}$N$_3$O.¼H$_2$O: Calculated: C, 55.81; H, 6.44; N, 16.27. Found: C, 55.98; H, 6.55; N, 16.10.

EXAMPLE X 2,3,4,4a-Tetrahydro-3-(2-Phenethyl)-1H-Pyrazino[1,2-a]Quinoxaline-5(6H)-One A mixture of 1.5 g. of 2,3,4,4a-tetrahydro-1H-pyrazino[1,2-a]quinoxaline-5(6H)-one, 3 ml. of phenethyl bromide, 2.0 g. of sodium iodide, 1.2 g. of potassium carbonate and 75 ml. acetone is refluxed for 20 hours under a nitrogen atmosphere. The mixture is concentrated, washed with ethyl acetate and filtered. The ethyl acetate filtrate is acidified with hydrogen chloride and filtered to give 1.6 g. of light tan solid. Recrystallization of the solid from ethanol-ether gives 1.1 g. of white solid product, m.p. 260°–263° dec.

Analysis for: C$_{19}$H$_{21}$N$_3$O.HCl.H$_2$O: Calculated: C, 63.10; H, 6.63; N, 11.69. Found: C, 62.78; H, 6.25; N, 11.60.

EXAMPLE XI

3-[4-(4-Fluorophenyl)-4-Oxobutyl]-2,3,4,4a-Tetrahydro-1H-Pyrazino[1,2-a]Quinoxalin-5(6H)-One A mixture of 1.3 g. of 2,3,4,4a-tetrahydro-1H-pyrazino[1,2-a]quinoxalin-5(6H)-one, 1.9 g. sodium iodide, 0.9 g. potassium carbonate, 2.6 g. of p-fluoro-γ-chloro butyrophenone and 50 ml. of acetone is refluxed for 20 hours under a nitrogen atmosphere. The reaction mixture is filtered and concentered. The residue is washed with ethyl acetate and filtered. The filtrate is acidified with hydrogen chloride and filtered to give 1.5 g. of solid product, m.p. 140°–180°. Recrystallization of the solid from ethanol-ether gives 0.85 g. of product, m.p. 145°–150°.

Analysis for: C$_{21}$H$_{23}$N$_3$O$_2$FCl.½H$_2$O: Calculated: C, 61.08; H, 5.85; N, 10.18. Found: C, 60.59; H, 5.69; N, 10.20.

EXAMPLE XII

4-Carbobenzoxy-1-(5-Methoxy-2-Nitrophenyl)Piperazine-2-Carboxylic Acid

By the same procedure described in Example VI, from 5.2 g. of 2-fluoro-4-methoxy nitrobenzene and 6.01 of 4-carbobenzoxypiperazine-2-carboxylic acid, hydrochloride, there is obtained 7.0 g. of product as an orange glass which is essentially pure by TLC analysis.

EXAMPLE XIII

3-Carbobenzoxy-2,3,4,4a-Tetrahydro-9-Methoxy-1H-Pyrazino[1,2-a]Quinoxalin-5(6H)-One By the same procedure described in Example VII, from 5.0 g. of 4-carbobenzoxy-1-(5-methoxy-2-nitrophenyl)piperazine-2-carboxylic acid there is obtained 3.1 g. of product, m.p. 167°–170°. Recrystallization from ethyl acetate gives an analytical sample, m.p. 173°–174°.

Analysis for: C$_{20}$H$_{21}$N$_3$O$_4$: Calculated: C, 65.38; H, 5.76; N, 11.44. Found: C, 65.42; H, 5.80; N, 11.53.

EXAMPLE XIV 2,3,4,4a-Tetrahydro-9-Methoxy-1H-Pyrazino[1,2-a]Quinoxalin-5(6H)-One By the same procedure described in Example VIII, from 3.2 g. of 3-carbobenzoxy-2,3,4,4a-tetrahydro-9-methoxy-1H-pyrazino[1,2-a]quinoxalin-5(6H)-one there is obtained, on recrystallization from ethanol-water, 1.85 g. of product as the hydrogen chloride salt, m.p. 275° dec.

Analysis for: $C_{12}H_{16}N_3O_2Cl$: Calculated: C, 53.43; H, 5.98; N, 15.58. Found: C, 53.00; H, 5.88; N, 15.38.

EXAMPLE XV

4-Carbobenzoxy-1-(4-Chloro-2-Nitrophenyl)Piperazine-2-Carboxylic Acid

By the same procedure described in Example VI, from 6.25 g. of 5-chloro-2-fluoronitrobenzene and 11 g. of 4-carbobenzoxypiperazin-2-carboxylic acid, hydrochloride, there is obtained 9.5 g. of product as an orange glass which is essentially pure by TLC analysis.

EXAMPLE XVI

3-Carbobenzoxy-8-Chloro-2,3,4,4a-Tetrahydro-1H-Pyrazino[1,2-a]Quinoxalin-5(6H)-One By the same procedure described in Example VII from 6.2 g. of 4-carbobenzoxy-1-(4-chloro-2-nitrophenyl)piperazine-2-carboxylic acid there is obtained 3.5 g. of product, m.p. 130°–140°, suitable for further use. In this case the product is isolated from the aqueous reaction mixture by extraction with ethyl acetate, drying the ethyl acetate over magnesium sulfate and removing the solvent under vacuum.

EXAMPLE XVII

8-Chloro-2,3,4,4a-Tetrahydro-1H-Pyrazino[1,2-a]Quinoxalin-5(6H)-One

By the same procedure described in Example VIII, from 3.0 g. of 3-carbobenzoxy-2,3,4,4a-tetrahydro-8-chloro-1H-pyrazino[1,2-a]quinoxalin-5(6H)-one there is obtained 0.95 g. of the product, as the hydrogen, chloride salt, m.p. 210° dec. on recrystallization from ethanol.

Analysis for: $C_{11}H_{13}N_3OCl_2.\frac{3}{4}H_2O$: Calculated: C, 45.94; H, 5.08; N, 14.61. Found: C, 46.34; H, 5.07; N, 14.21.

EXAMPLE XVIII

2-Chloro-6-Fluoroaniline

To a stirred mixture of 20 g. of 2-chloro-6-fluorobenzoic acid, 100 ml. of chloroform and 50 ml. of concentrated sulfuric acid is added slowly 10.2 g. of sodium azide while the temperature is kept at 40°–55°. Stirring is continued for 2 hours at 40°–55° then the mixture is poured into 500 ml. of ice water containing 80 g. of sodium hydroxide. The mixture is extracted with ether and the other extracts are dried over magnesium sulfate. The dry extracts are then treated with hydrogen chloride, and the resultant product as the hydrochloride salt is collected by filtration yielding 12.6 g. of white solid which sublimes at 160°–170°.

EXAMPLE XIX

2-Chloro-6-Fluoronitrobenzene

To a solution of 17.2 g. of 2-chloro-6-fluoroaniline hydrochloride and 12.5 ml. of concentrated hydrochloric acid in 150 ml. of water is added slowly a solution of 9 g. of sodium nitrate in 25 ml. of water. The temperature of the solution of kept below 5° at all times. This solution is then added to a stirred suspension of 18 g. of cuprocupric sulfate and 60 g. of sodium nitrate in 300 ml. of water at room temperature. The mixture is stirred for 1 hour then steam distilled until no trace of product is noted condensing in the distillate. The distillate is extracted with ether, dried (magnesium sulfate) concentrated and distilled to give 7.8 g. of product, b.p. 148°–152° at 30 mm. Gas chromatography analysis shows this to be greater than 95% pure.

EXAMPLE XX

4-Carbobenzoxy-1-(3-Chloro-2-Nitrophenyl)Piperazine-2-Carboxylic Acid

By the same procedure described in Example VI, from 6.5 g. of 2-chloro-6-fluoronitrobenzene and 12 g. of 4-carbobenzoxypiperazine-2-carboxylic acid, hydrochloride, there is obtained 9 g. of product as a pale yellow glass which is essentially pure by TLC analysis.

EXAMPLE XXI

3-Carbobenzoxy-7-Chloro-2,3,4,4a-Tetrahydro-1H-Pyrazino[1,2-a]Quinoxalin-5(6H)-One By the same procedure described in Example VII, from 4.5 g. of 4-carbobenzoxy-1-(3-chloro-2-nitrophenyl)piperazine there is obtained 3.5 g. of product, m.p. 178°–182°. Recrystallization from ethanol gives an analytical sample, m.p. 189°–191°.

Analysis for: $C_{19}H_{18}N_3O_3Cl$: Calculated: C, 61.37; H, 4.88; N, 11.30. Found: C, 60.81; H, 5.03; N, 11.27.

EXAMPLE XXII

7-Chloro-2,3,4,4a-Tetrahydro-1H-Pyrazino[1,2-a]Quinoxalin-5(6H)-One

By the same procedure described in Example VIII, from 3.2 g. of 3-carbobenzoxy-2,3,4,4a-tetrahydro-7-chloro-1H-pyrazino[1,2-a]quinoxalin-5(6H)-one there is obtained on recrystallization from ethanol-water 1.0 g. of the product as the hydrogen chloride salt, m.p. 270°–275° dec.

Analysis for: $C_{11}H_{12}N_3OCl.HCl.H_2O$: Calculated: C, 45,22; H, 5.18; N, 14.38. Found: C, 45.55; H, 4.76; N, 14.41.

EXAMPLE XXIII

4-Fluoro-3-Nitrotoluene

By a procedure analogous to that described in Example XIX, from 10 g. of 4-fluoro-3-aminotoluene there is obtained 4.2 g. of nitro product as a pale yellow liquid, b.p. 105° to 110° at 25 mm.

EXAMPLE XXIV

4-Carbobenzoxy-1-(4-Trifluoromethyl-2-Nitrophenyl)-Piperazine-2-Carboxylic Acid

By a procedure analogous to that described in Example VI, from 10 g. of 2-chloro-5-trifluoromethylnitrobenzene and 12 g. of 4-carbobenzoxypiperazine-2-carboxylic acid, hydrochloride, there is obtained 14 g. of product as a dark orange glass which is essentially pure by TLC analysis.

EXAMPLE XXV 2,3,4,4a-Tetrahydro-8-Trifluoromethyl-1H-Pyrazino[1,2-a]Quinoxalin-5(6H)-One A solution of 7.5 g. of 4-carbobenzoxy-1-(4-trifluoromethyl-2-nitrophenyl)piperazine-2-carboxylic acid, 4.0 g. of potassium bicarbonate, 150 ml. of water and 50 ml. of ethanol is hydrogenated over three teaspoons of Raney nickel catalyst at 50 p. s. i. for 45 minutes. The catalyst is filtered and the filtrate is acidified and extracted with ethylacetate. The aqueous phase is then basified with dilute sodium hydroxide and extracted with ethyl acetate. Concentration of the organic phase gives 1.2 g. of pale yellow solid product, m.p. 193–195°. This solid is converted to its hydrogen chloride salt in ethanol giving 0.78 g., m.p. 275–277° dec.

Analysis for: $C_{12}H_{12}N_3OF_3 \cdot 1\frac{1}{4} H_2O$: Calculated: C, 59.26; H, 4.48; N, 10.37. Found: C, 58.74; H, 4.61; N, 10.12.

EXAMPLE XXVI

3-Carbobenzoxy-2,3,4,4a-Tetrahydro-8-Trifluoromethyl-1H-Pyrazino[1,2-a]Quinoxalin-5(6H)-One By the same procedure described in Example VII, from 3.5 g. of 4-carbobenzoxy-1-(4-trifluoromethyl-2-nitrophenyl)piperazine-2-carboxylic acid there is obtained 1.2 g. of crude product with m.p. 170–175°. Recrystallization from ethanol gives product with m.p. 201–204°.

Analysis for: $C_{20}H_{18}N_3O_3F_3$: Calculated: C, 59.26; H, 4.48; N, 10.37. Found: C, 58.74; H, 4.61; N, 10.12.

EXAMPLE XXVII

4-Carbobenzoxy-1-(5-Chloro-2-Nitrophenyl)Piperazine-2-Carboxylic Acid

By a procedure analogous to that described in Example VI, from 7.7 g. of 2,4-dichloronitrobenzene and 6.0 g. of 4-carbobenzoxypiperazine-2-carboxylic acid, hydrochloride there is obtained 5.0 g. of yellow orange glass which showed one main yellow spot and one lesser spot on TLC analysis.

EXAMPLE XXVIII

3-Carbobenzoxy-9-Chloro-2,3,4,4a-Tetrahydro-1H-Pyrazino[1,2-a]Quinoxalin-5(6H)-One By the same procedure described in Example VII, from 5.0 g. of 4-carbobenzoxy-1-(5-chloro-2-nitrophenyl)piperazine-2-carboxylic acid, there is obtained 1.0 g. of product as a tan solid. Recrystallization from ethanol gives product, m.p. 188–191°.

EXAMPLE XXIX

9-Chloro-2,3,4,4a-Tetrahydro-1H-Pyrazino[1,2-a]Quinoxalin-5(6H)-One

By the same procedure described in Example VIII, from 1.9 g. of 3-carbobenzoxy-2,3,4,4a-tetrahydro-9-chloro-1H-pyrazino[1,2-a]quinoxalin-5(6H)-one there is obtained on recrystallization from ethanol 0.40 g. of the product as the hydrogen chloride salt, m.p. 300–303°.

Analysis for: $C_{11}H_{12}N_3OCl \cdot H_2O \cdot \frac{1}{2} C_2H_5OH$: Calculated: C, 45.35; H, 5.33; N, 14.10. Found: C, 45.28; H, 4.90; N, 13.66.

EXAMPLE XXX

2-Nitro-4-Trifluoroacetamidofluorobenzene

To a stirred solution of 7.8 g. of 4-fluoro-3-nitroaniline, 5.0 g. of triethylamine in 150 ml. of methylene chloride is added dropwise 10.5 g. of trifluoroacetic anhydride at 5° to 10°. The mixture is stirred for 0.5 hours, washed with water, dried and concentrated to give a brown oil which crystallizes. Recrystallization from benzene cyclohexane gives 5.3 g. of product, m.p. 70–75°.

EXAMPLE XXXI

4-Carbobenzoxy-1-(2-nitro-4-Trifluoroacetamidophenyl)Piperazine-2-Carboxylic Acid By a procedure analogous to that described in Example VI, from 5.0 g. of 2-nitro-4-trifluoroacetamido fluorobenzene and 6.0 g. of 4-carbobenzoxypiperazine-2-carboxylic acid, hydrochloride there is obtained 8.5 g. of yellow orange solid, m.p. 212–215°. TLC analysis shows 1 spot.

EXAMPLE XXXII

3-Carbobenzoxy-2,3,4,4a-Tetrahydro-8-(2,2,2-Trifluoroacetamido)-1H-Pyrazino[1,2-a]-Quinoxalin-5(6H)-One By a procedure analogous to that described in Example VII from 4.6 g. of 4-carbobenzoxy-1-(2-nitro-2-trifluoroacetamidophenyl)piperazine-2-carboxylic acid, there is obtained 3.6 g. of product, m.p. 255–262°. Recrystallization from ethanol-water gives 2.75 g., m.p. 264–265°.

Analysis for: $C_{21}H_{19}N_4O_4F_3$: Calculated: C, 56.24; H, 4.27; N, 12.50. Found: C, 56.02; H, 4.46; N, 12.65.

EXAMPLE XXXIII 2,3,4,4a-Tetrahydro-8-(2,2,2-Trifluoroacetamido)-1H-Pyrazino[1,2-a]Quinoxalin-5(6H)-One By an analogous procedure to that described in Example VIII, from 2.2 g. of 3-carbobenzoxy-2,3,4,4a-tetrahydro-8-(2,2,2-trifluoroacetamido)-1H-pyrazino[1,2-a]quinoxalin-5(6H)-one there is obtained 0.46 g. of the product as the hydrogen chloride salt, m.p. 316–318° dec.

Analysis for: $C_{13}H_{14}N_4O_2F_3Cl \cdot \frac{1}{2}H_2O$: Calculated: C, 43.40; H, 4.20; N, 15.57. Found: C, 43.64; H, 3.87; N, 15.35.

EXAMPLE XXXIV

8-Amino-3-Carbobenzoxy-2,3,4,4a-Tetrahydro-1H-Pyrazino]1,2-a]Quinoxalin-5(6H)-One A mixture of 2.8 g. of 3-carbobenzoxy-2,3,4,4a-Tetrahydro-8-(2,2,2-trifluoroacetamido)-1H-pyrazino[1,2-a]quinoxalin5(6H)-one, 0.5 g. sodium hydroxide and 200 ml. of water is boiled for 15 minutes, then cooled. The mixture is then extracted with methylene chloride. The organic portion is then extracted with dilute hydrochloric acid. The aqueous acid phase is then basified with dilute sodium hydroxide and extracted with methylene chloride. The organic phase is dried and concentrated to give 1.6 g. of pale yellow solid product, m.p. 130–135°.

EXAMPLE XXXV

8-Amino-2,3,4,4a-Tetrahydro-1H-Pyrazino[1,2-a]Quinoxalin-5(6H)-One

A mixture of 1.5 g. of 8-amino-3-carbobenzoxy-2,3,4,4a-tetrahydro-1H-pyrazino[1,2-a]quinoxalin-5(6H)-one, 1.5 g. of 10% Palladium on carbon catalyst and 150 ml. of ethanol is hydrogenated for ½ hour at 45 p. s. i. The catalyst is filtered and the filtrate concentrated to a volume of 50 ml. Ethanolic hydrochloric acid is added, and the product precipitates as the hydrochloride salt. Weight of product 0.70 g., m.p. 294–295° dec. Recrystallization from ethanol-water gives 0.45 g. of pure product, m.p. 315–317° dec.

Analysis for: $C_{11}H_{16}N_4OCl_2$: Calculated: C, 45.37; H, 5.54; N, 19.24. Found: C, 45.25; H, 5.71; N, 18.80.

EXAMPLE XXXVI

4-Carbobenzoxy-1-(5-Methyl-2-Nitrophenyl)-2-Carboxylic Acid

By a procedure analogous to that described in Example VI, from 7.0 g. of 3-fluoro-4-nitrotoluene and 12.0 g. of 4-carbobenzoxypiperazine-2-carboxylic acid, hydrochloride, there is obtained 15.0 g. of yellow-orange glass which is essentially pure by TLC analysis.

EXAMPLE XXXVII

3-Carbobenzoxy-2,3,4,4a-Tetrahydro-9-Methyl-1H-Pyrazino[1,2-a]Quinoxalin-5(6H)-One By the same procedure described in Example VII from 15 g. of 4-carbobenzoxy-1-(5-methyl-2-nitrophenyl)piperazine-2-carboxylic acid there is obtained 8.00 g. of colorless product which on recrystallization from ethanol gives product with m.p. 175–178°.

Analysis for: $C_{20}H_{21}N_3O_3 \cdot \frac{1}{2}H_2O$: Calculated: C, 66.63; H, 6.15; N, 11.66. Found: C, 66.16; H, 5.98; N, 11.45.

EXAMPLE XXXVIII

2,3,4,4a-Tetrahydro-9-Methyl-1H-Pyrazino[1,2-a]Quinoxalin-5(6H)-One

By the same procedure described in Example VIII from 6.0 g. of 3-carbobenzoxy-2,3,4,4a-tetrahydro-9-methyl-1H-pyrazino[1,2-a]quinoxalin-5(6H)-one there is obtained 0.93 g. of the hydrogen chloride salt of the product with m.p. 195° dec.

Analysis for: $C_{12}H_{16}N_3O \cdot HCl$: Calculated: C, 56.80; H, 6.36; N, 16.56. Found: C, 56.32; H, 6.28; N, 16.30.

EXAMPLE XXXIX

4-Carbobenzoxy-1-(4-Fluoro-2-Nitrophenyl)-2-Carboxylic Acid

By a procedure analogous to that described in Example VI, from 6.5 g. of 2,5-difluoronitrobenzene and 12.0 g. of 4-carbobenzoxypiperazine-2-carboxylic acid, hydrochloride, there is obtaine 14 g. of yellow-orange glass which is essentially pure by TLC analysis.

EXAMPLE XL

3-Carbobenzoxy-2,3,4,4a-Tetrahydro-8-Fluoro-1H-Pyrazino[1,2-a]Quinoxalin-5(6H)-One 3-Carbobenzoxy-2,3,4,4a-tetrahydro-8-fluoro-1H-pyrazino[1,2-a]quinoxalin-5(6H)-one is prepared bt essentially the same procedure described by Example VII. In this example, however, the product is extracted from the aqueous reaction mixture (after acidification) with ethyl acetate, dried and concentrated to give 6 g. of crude product. Recrystallization of the product from ethanol gives 4.8 g. of product with m.p. 173°–175°.

Analysis for: $C_{19}H_{18}N_3O_3F$: Calculated: C, 64.21; H, 5.12; N, 11.62. Found: C, 63.97; H, 5.16; N, 11.69.

EXAMPLE XLI

2,3,4,4a-Tetrahydro-8-Fluoro-1H-Pyrazino[1,2-a]Quinoxalin-5(6H)-One

By the same procedure described in Example VIII, from 4.5 g. of 3-carbobenzoxy-2,3,4,4a-tetrahydro-8-fluoro-1H-pyrazino[1,2-a]quinoxalin-5(6H)-one there is obtained 2.20 g. of the hydrogen chloride salt of the product with m.p. 266–270° dec.

Analysis for: $C_{11}H_{12}N_3OF \cdot HCl$: Calculated: C, 51.26; H, 5.08; N, 16.30. Found: C, 50.90; H, 5.19; N, 16.00.

EXAMPLE XLII

By procedures analogous to those described in Examples XXXIX, XL, and XLI, using 2,6-difluoronitrobenzene or 2,4-difluoronitrobenzene as starting materials there are produced, respectively, 2,3,4,4a-tetrahydro-7-fluoro-1H-pyrazino[1,2-a]quinoxalin-5(6H)-one and 2,3,4,4a-tetrahydro-9-fluoro-1H-pyrazino[1,2-a]quinoxalin-5(6H)-one.

EXAMPLE XLIII

3-Carbobenzoxy-2,3,4,4a-Tetrahydro-1H-Pyrazino[1,2-a]Quinoxalin-5(6H)-One

A solution of 4-carbobenzoxy-1-(o-nitrophenyl)piperazine-2-carboxylic acid (Ex. VI), 28 gms. (0.073 mole) in 300 ml. ether was extracted with 600 ml. (3 × 200 ml. portions) of aqueous 2% sodium bicarbonate solution. The ether layer was then washed with 500 ml. water. The aqueous layer was added to the bicarbonate extracts. The ether layer was discarded. The combined aqueous extracts were diluted to 2 liters. To this stirred solution was added 30 gms. of sodium dithionite ($Na_2S_2O_4$). The reddish solution turned nearly white and a precipitate formed (pH ~7). After stirring for five minutes the pH was adjusted to ~5 with 20% HCl. The pH was raised to about 7, and the product was filtered, washed with cold water, and dried, yielding 15 gms. of product, m.p. 168–170°.

Analysis for: $C_{19}H_{19}N_3O_3$: Calculated: C, 67.64; H, 5.68; N, 12.46. Found: C, 67.44; H, 5.82; N, 12.30.

EXAMPLE XLIV

4-Carbobenzoxy-1-(4-Methyl-2-Nitrophenyl)Piperazine-2-Carboxylic Acid

By a procedure analogous to that described in Example VI, from 4.0 g. of 4-fluoro-3-nitrotoluene and 7.5 g. of 4-carbobenzoxypiperazine-2-carboxylic acid, hydrochloric, there is obtained 3.0 g. of product as an orange glass which is essentially pure by TLC analysis.

EXAMPLE XLV

3-Carbobenzoxy-2,3,4,4a-Tetrahydro-8-Methyl-1H-Pyrazino[1,2-a]Quinoxalin-5(6H)-One By the same procedure described in Example VII from 3.0 g. of 4-carbobenzoxy-1-(4-methyl-2-nitrophenyl)piperazine-2-carboxylic acid there is obtained 1.7 g. of product as a pale yellow glass which partially crystallizes. TLC analysis shows only one spot.

EXAMPLE XLVI

2,3,4,4a-Tetrahydro-8-Methyl-1H-Pyrazino[1,2-a]Quinoxalin-5(6H)-One

By the same procedure described in Example VIII from 1.6 g. of 3-carbobenzoxy-2,3,4,4a-tetrahydro-8-methyl-1H-pyrazino[1,2-a]quinoxalin-5(6H)-one there is obtained 0.60 g. of the hydrogen chloride salt of the product with m.p. 296–298° dec. on recrystallization from ethanol.

Analysis for: $C_{12}H_{16}N_3O \cdot \frac{1}{4} H_2O$: Calculated: C, 55.81; H, 6.44; N, 16.27. Found: C, 55.82; H, 6.47; N, 15.92.

EXAMPLE XLVII

The antihypertensive effect of a compound of Formula Ia or Ib is ellicited and demonostrated by administering the compound to a hypertensive rat and measuring the change in systolic blood pressure 2 and 4 hours after administration. The rats used are either spontaneously hypertensive or are rendered hypertensive by applying a figure-of-eight ligature around one kidney and contralateral nephrectomy. Male spontaneously hypertensive rats derived from the Okamoto-Aoki strain were purchased from commercial breeders. In the renal hypertensive rats, blood pressure tends to stabilize at a hypertensive level after approximately six weeks. A group of at least 4 rats is given the compound by the oral (P.O.) route. Systolic blood pressure, as measured by an indirect technique using the Decker Caudal Plethysmorgraph, is measured prior to administration of the compound and at 2 and 4 hours thereafter. This schedule may vary depending upon the behavior of the compound. A control group of rats, given either a placebo or a standard antihypertensive agent is run with each group of treated rats.

The hypotensive activity of the compound is rated as follows:

| Activity | Systolic Decrease in Blood Pressure |
|---|---|
| Slight | 25 – 35 mm Hg |
| Moderate | 35 – 50 |
| Marked | over 50 |

When tested as described above, the compounds of Formula Ia or Ib gave the following results:

| Compound | Activity (P.O.) |
|---|---|
| 2,3,4,4a-3-methyl-1H-pyrazino-[1,2-a]quinoxalin-5(6H)-one | Moderate at 20 mg/kg * |
| 2,3,4,4a,5,6-hexahydro-3-methyl 1H-pyazino]1,2-a]quinoxaline | Moderate at 50 mg/kg * |
| 2,3,4,4a-tetrahydro-3-(2-phenylethyl)-1H-pyrazino∥,2-a]quinoxalin-5(6H)-one | Moderate at 50 mg/kg ** |
| 3-[4-(4-fluorophenyl)-4-oxobutyl]-a]quinoxalin-5(6H)-one | Marked at * |
| 2,3,4,4a-tetrahydro-6-methyl-1H-pyrazino[1,2-a]quinoxalin-5(6H)-one | Marked at 5 mg/kg ** |
| 2,3,4,4a-tetrahydro-1H-pyrazino-[1,2-a]quinoxalin-5(6H)-one | Marked at 2.5 mg/kg ** |
| 2,3,4,4a-tetrahydro-9-methoxy-1H-pyrazino[1,2-a]quinoxalin-5(6H)-one | Slight at 10 mg/kg * |
| 7-chloro-2,3,4,4a-tetrahydro-1H-pyrazino[1,2-a]quinoxalin-5(6H)-one | Moderate at 10 mg/kg * |
| 8-chloro-2,3,4,4a-tetrahydro-1H-pyrazino[1,2-a]quinoxalin-5(6H)-one | Slight at 10 mg/kg * |
| 9-chloro-2,3,4,4a-tetahydro-1H-pyrazino[1,2-a]quinoxalin-5(6H)-one | Moderate at 5 mg/kg ** |
| 2,3,4,4a-tetrahydro-8-trifluoromethyl-1H-pyazino[1,2-a]quinoxalin-5(6H)-one | Slight at 5 mg/kg ** |
| 2,3,4,4a-tetrahydro-9-methyl-1H-pyrazino[1,2-a]quinoxalin-5(6H)-one | Slight at 2.5 mg/kg ** |
| 2,3,4,4a-tetrahydro-9-methyl-1H-pyrazino[1,2-a]quinoxalin-5(6H)-one | Slight at 2.5 mg/kg ** |

| Compound | Activity (P.O.) |
|---|---|
| 2,3,4,4a-tetrahydro-8-methyl-1H-pyrazino[1,2-a]quinoxalin-5(6H)-one | Slight at 10 mg/kg **(at 24 hrs) |
| 8-amino-2,3,4,4a-tetrahydro-1H-pyrazino[1,2-a]quinoxalin-5(6H)-one | Moderate at 75 mg/kg; Borderline at 25 mg/kg ** |
| 8-fluoro-2,3,4,4a-tetrahydro-1H-pyrazino[1,2-a]quinoxalin-5(6H)-one | Marked at 2.5 mg/kg ** |

* in renal hypertensive rats
** in spontaneously hypertensive rats

What is claimed is:

1. A compound of the formula:

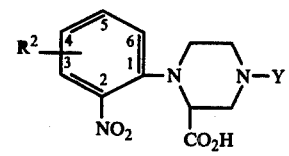

wherein:
Y is carbobenzoxy; and
$R^2$ is hydrogen, (lower)alkyl, (lower)alkoxy, chlorine, fluorine, trifluoromethyl, or trifluoroacetamido in the 3-, 4-, or 5-position of the phenyl ring; or the salts thereof.

2. The compound as defined in claim 1 which is 4-carbobenzoxy-1-(o-nitrophenyl)piperazine-2-carboxylic acid.

3. A compound as defined in claim 1 which is 4-carbobenzoxyl-1-(3-chloro-2-nitrophenyl)piperazine-2-carboxylic acid.

4. A compound as defined in claim 1 which is 4-carbobenzoxy-1-(4-chloro-2-nitrophenyl)piperazine-2-carboxylic acid.

5. A compound as defined in claim 1 which is 4-carbobenzoxy-1-(5-chloro-2-nitrophenyl)piperazine-2-carboxylic acid.

6. A compound as defined in claim 1 which is 4-carbobenzoxy-1-(4-methoxy-2-nitrophenyl)piperazine-2-carboxylic acid.

7. A compound as defined in claim 1 which is 4-carbobenzoxy-1-(5-methyl-2-nitrophenyl)piperazine-2-carboxylic acid.

8. A compound as defined in claim 1 which is 4-carbobenzoxy-1-(5-methoxy-2-nitrophenyl)piperazine-2-carboxylic acid.

9. A compound as defined in claim 1 which is 4-carbobenzoxy-1-(2-nitro-4-trilufluoroacetamidophenyl)-piperazine-2-carboxylic acid.

10. A compound as defined in claim 1 which is 4-carbobenzoxy-1-(4-trifluoromethyl-2-nitrophenyl)piperazine-2-carboxylic acid.

11. A compound as defined in claim 1 which is 4-carbobenzoxy-1-(4-fluoromethyl-2-nitrophenyl)piperazine-2-carboxylic acid.

* * * * *